(12) United States Patent
Shi

(10) Patent No.: US 8,779,155 B2
(45) Date of Patent: Jul. 15, 2014

(54) 1,2,3-TRIAZOLE BASED METAL-ORGANIC FRAMEWORK AS PHOTO-ACTIVE MATERIALS

(75) Inventor: Xiaodong Shi, Morgantown, WV (US)

(73) Assignee: West Virginia University, Morgantown, WV (US)

( * ) Notice: Subject to any disclaimer, the term of this patent is extended or adjusted under 35 U.S.C. 154(b) by 287 days.

(21) Appl. No.: 13/068,489

(22) Filed: May 12, 2011

(65) Prior Publication Data

US 2011/0282071 A1    Nov. 17, 2011

Related U.S. Application Data

(60) Provisional application No. 61/395,341, filed on May 12, 2010.

(51) Int. Cl.
*C07D 249/06* (2006.01)

(52) U.S. Cl.
USPC .......................................................... 548/255

(58) Field of Classification Search
None
See application file for complete search history.

(56) References Cited

U.S. PATENT DOCUMENTS 3,666,758 A * 5/1972 Dorlars et al. ................ 548/255

FOREIGN PATENT DOCUMENTS

DE    1917740 A    * 10/1970

OTHER PUBLICATIONS

Yan, W. et al., N-2-Aryl-1,2,3-triazoles: A Novel Class of UV/Blue-Light-Emitting Fluorophores with Tunable Optical Properties, Chemistry, Chem Eur J., 2011, 5011-5018, vol. 17, Wiley-VCH Verlag GmbH & Co. KGaA, Weinheim.

* cited by examiner

*Primary Examiner* — Kamal Saeed
(74) *Attorney, Agent, or Firm* — Buchanan Ingersoll & Rooney PC; Craig G. Cochenour

(57) ABSTRACT

A TAF compound that can have substitutions on either of the two benzene rings and/or the C-5 position of the triazole to alter the properties of the TAF compound can be

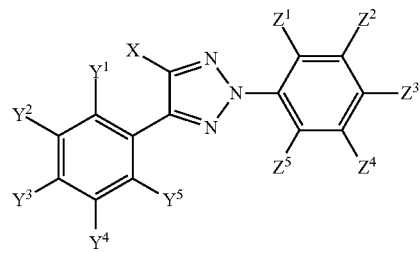

wherein X can be H, an aromatic group, a hetero aromatic group, an alkyl or any substituted alkyl group, ketone, aldyhyde, carboxylic acid derivatives; $Y^1, Y^2, Y^3, Y^4$, and $Y^5$ can be one or more of H, aromatic groups, hetero aromatic groups, alkyl or any substituted alkyl groups, ketone, aldyhyde, or carboxylic acid derivatives; and $Z^1, Z^2, Z^3, Z^4$, and $Z^5$ can be one or more of H aromatic groups, hetero aromatic groups, alkyl or any substituted alkyl groups, ketone, aldyhyde, or carboxylic acid derivatives. Included is a preparation of the TAF compound and use as a photoactive and/or catalyst.

1 Claim, 2 Drawing Sheets

1,2,3-TRIAZOLE BASED METAL-ORGANIC FRAMEWORK AS PHOTO-ACTIVE MATERIALS

CROSS-REFERENCE TO RELATED APPLICATIONS

This application claims priority to provisional application numbered 61/395,341 filed on May 12, 2010.

REFERENCE TO SEQUENCE LISTING, A TABLE, OR A COMPUTER PROGRAM LISTING COMPACT DISC APPENDIX

Not Applicable

DETAILED DESCRIPTION OF THE INVENTION

A first embodiment can be triazole-modified compound TAF. The TAF compound can have substitutions on either of the two benzene rings and/or the C-5 position of the triazole to alter the properties of the TAF. The TAF compound can be

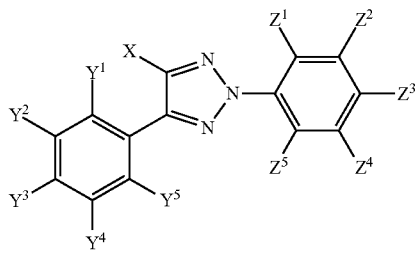

wherein X can be H, an aromatic group, a hetero aromatic group, an alkyl or any substituted alkyl group, ketone, aldyhyde, carboxylic acid derivatives; $Y^1$, $Y^2$, $Y^3$, $Y^4$, and $Y^5$ can be one or more of H, aromatic groups, hetero aromatic groups, alkyl or any substituted alkyl groups, ketone, aldyhyde, or carboxylic acid derivatives; and $Z^1$, $Z^2$, $Z^3$, $Z^4$ and $Z^5$ can be one or more of H aromatic groups, hetero aromatic groups, alkyl or any substituted alkyl groups, ketone, aldyhyde, or carboxylic acid derivatives.

TAF can be prepared from bifunctional 1,2,3-triazoles by treatment with $Zn(NO_3)_2$. About 1-5 mmol of the 1,2,3-triazole solutions wherein the solvents can be water, acetonitrile, DMSO, DMF, DEF, any alcohol, THF. This solution can be added to about 1-5 mmol $Zn(NO_3)_2$ solutions at a concentration between about 0.1 mmol to about 2 mol wherein the solvents can be water, acetonitrile, DMSO, DMF, DEF, any alcohol, THF. The solutions can be kept at an effective temperature which can range from about room temperature to about 180° C. for an effective time from about 1 hour to about 7 days to prepare TAF.

Figure 2:
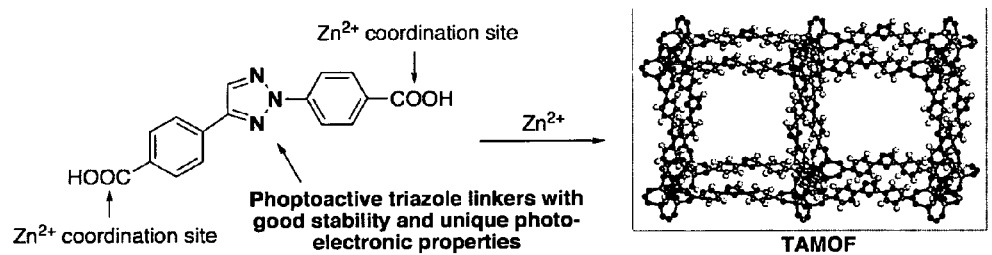
FIG. 2 is the reaction for TAMOF production.

FIG. 2 details the TAMOF preparation. The Zn2+ coordination sites are on the COOH sites of the tirazole while the Ns provide photoactive triazole linkers with good stability and unique photoelectronic properties.

Figure 1:
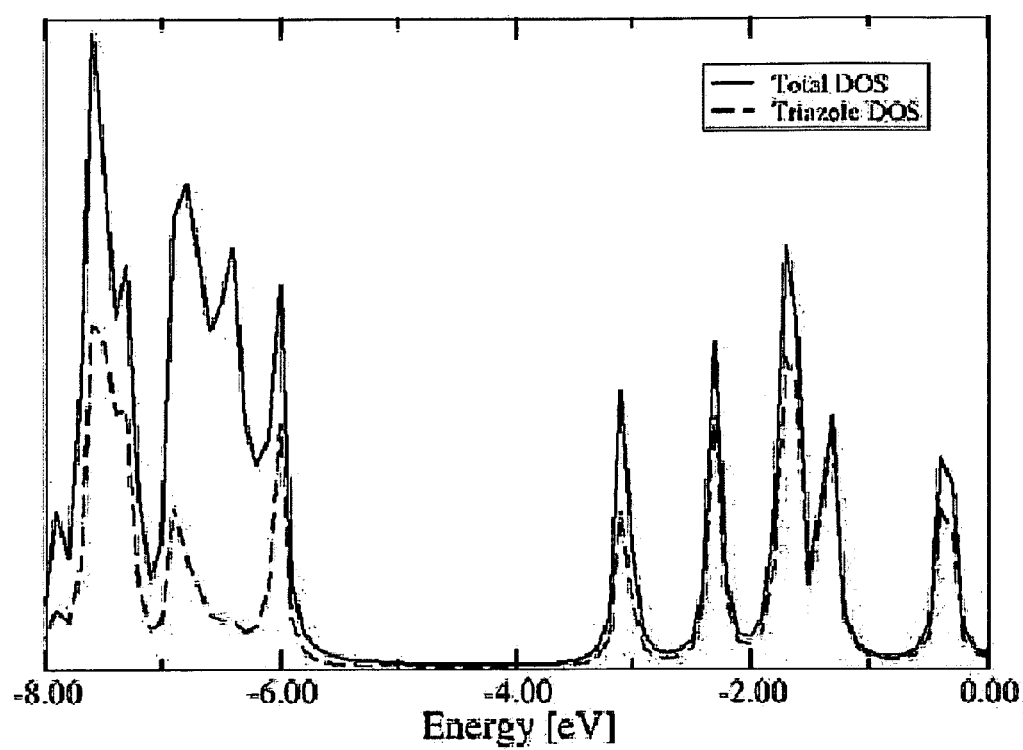
FIG. 1 is a representative structure of the ligand design and modification.

The TAF compound can be used as a photoactive material and/or catalyst. The absorption wavelength could be easily adjusted by the substitution of different aryl groups such as F, CN, Cl, OMe, phenyl, or heteroaromatic structures on the TAF compound. The N-aryl triazoles possess unique molecular orbital distributions. This feature makes the preparation of solar-light absorbing linkers for the preparation of metal-organic frameworks feasible. The orbital distribution made triazole one unique compound to express interesting photo and electronic properties. TAF has a band gap around 2.8 eV which is optimal for a photocatalysis as seen in FIG. 1. The HOMO and LUMO were confirmed locating on the triazole ring and H-bonding between C-4-H and $CO_2$ was revealed with a calculated 17 kcal/mol of binding energy.

These terms and specifications, including the examples, serve to describe the invention by example and not to limit the invention. It is expected that others will perceive differences, which, while differing from the forgoing, do not depart from the scope of the invention herein described and claimed. In particular, any of the function elements described herein may be replaced by any other known element having an equivalent function.

What is claimed is:

1. A compound comprising

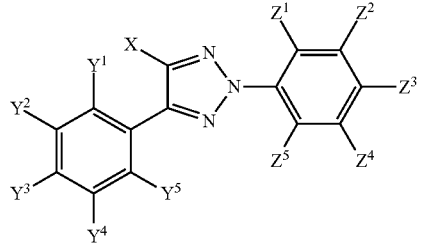

wherein X is H, $Y^1$, $Y^2$, $Y^4$, and $Y^5$ are each H, $Z^1$, $Z^2$, $Z^4$ and $Z^5$ are each H, and $Y^3$ and $Z^3$ are each COOH.

* * * * *